United States Patent
Halseth et al.

(10) Patent No.: US 6,607,511 B2
(45) Date of Patent: Aug. 19, 2003

(54) MEDICAL DEVICE WITH SAFETY FLEXIBLE NEEDLE

(75) Inventors: Thor R. Halseth, Simi Valley, CA (US); Robert T. McWethy, Ventura, CA (US); John Barker, Ventura, CA (US)

(73) Assignee: MDC Investment Holdings, Inc., Wilmington, DE (US)

(*) Notice: Subject to any disclaimer, the term of this patent is extended or adjusted under 35 U.S.C. 154(b) by 0 days.

(21) Appl. No.: 09/925,933

(22) Filed: Aug. 9, 2001

(65) Prior Publication Data

US 2003/0032927 A1 Feb. 13, 2003

(51) Int. Cl.[7] .............................................. A61M 5/178
(52) U.S. Cl. ................................................ 604/164.08
(58) Field of Search ................................. 604/110, 158, 604/161, 163, 164.01, 164.06, 164.07, 164.09, 164.1, 164.11, 164.12, 164.13, 165.01, 165.02, 181, 187, 195, 198, 192, 263–264, 272, 239; 128/917, 919

(56) References Cited

U.S. PATENT DOCUMENTS

| | | | |
|---|---|---|---|
| 3,539,034 A | * 11/1970 | Tafeen | 604/164.09 |
| 3,565,074 A | * 2/1971 | Foti | 604/164.11 |
| 3,884,230 A | 5/1975 | Wulff | |
| 4,676,249 A | 6/1987 | Arenas et al. | |
| 4,850,960 A | 7/1989 | Grayzel | |
| 4,886,067 A | 12/1989 | Palermo | |
| 4,886,500 A | 12/1989 | Lazarus | |
| 4,917,102 A | 4/1990 | Miller et al. | |
| 4,955,862 A | 9/1990 | Sepetka | |
| 4,961,729 A | * 10/1990 | Vaillancourt | 604/168.01 |
| 5,060,658 A | * 10/1991 | Dejter et al. | 600/566 |
| 5,779,680 A | * 7/1998 | Yoon | 604/158 |
| 5,788,654 A | 8/1998 | Schwager | |
| 5,910,133 A | * 6/1999 | Gould | 604/170.03 |
| 5,916,194 A | * 6/1999 | Jacobsen et al. | 604/96.01 |
| 5,935,108 A | 8/1999 | Katoh et al. | |

* cited by examiner

Primary Examiner—Brian L. Casler
Assistant Examiner—LoAn H. Thanh
(74) Attorney, Agent, or Firm—Stephen H. Eland; Dann, Dorfman, Herrell and Skillman

(57) ABSTRACT

A device is provided for inserting medical instruments, such as pacemaker leads, into a patient. The device includes a flexible needle with a sharpened tip surrounded by a sheath and catheter. A biasing element biases the needle toward a position in which the needle tip is enclosed within the sheath. A method for inserting a medical instrument, such as a pacemaker lead, is also provided, in which the needle is inserted into a patient, followed by the sheath and catheter. The needle is then retracted so that the sharpened tip is enclosed within the sheath. The needle remains in the sheath as the sheath and catheter are curved into alignment with a blood vessel and advanced through the blood vessel. The needle and sheath are then pulled out, and a pacemaker lead or other instrument is fed through the catheter and into the vessel.

20 Claims, 8 Drawing Sheets

MEDICAL DEVICE WITH SAFETY FLEXIBLE NEEDLE

FIELD OF THE INVENTION

The present invention relates to medical devices for inserting medical instruments into a patient's blood vessel. In particular, the present invention relates to medical devices having a sharpened flexible needle for inserting a medical instrument, such as a pacemaker lead, into a patient's blood vessel. The flexible needle pierces the patient to provide vascular access. After vascular access is established, the flexible needle is retracted into a flexible sheath and catheter that surround the needle. The flexible needle remains inside the sheath as the sheath and catheter are bent into alignment with the blood vessel and advanced into the blood vessel. Once the catheter is set properly within the blood vessel, the sheath and retracted needle are pulled out from the patient leaving the catheter within the patient's blood vessel. A pacemaker lead or other medical instrument is inserted into the catheter and advanced through the catheter into the patient's body. The catheter is then removed.

BACKGROUND

The insertion of pacemaker leads and other elements into the heart region requires piercing the skin with a needle device to provide access to blood vessels. The process for inserting pacemaker leads into the heart begins with the insertion of a needle set into the upper chest. The needle set, which includes a sharpened needle surrounded by a dilator sheath and a catheter, is inserted into a vein in the upper chest, such as the subclavian vein. When the needle tip has accessed the vein, blood flows out the back of the device. Consequently, a syringe or other blood collection device is attached to the needle set to prevent the blood flow from leaking out the device onto the medical professional.

The sharpened needle is typically a rigid needle. As a result, the needle set is relatively stiff. To facilitate insertion of the pacemaker lead, the needle set must be carefully turned while it is in the subclavian vein so that the passage in the needle set is aligned with the axis of the blood vessel. After alignment is achieved, the syringe is removed from the rear end of the device. A guidewire is then fed through the open rear end of the device and needle set into the subclavian vein. The guidewire is advanced down the subclavian vein to a position above the right atrium of the heart. The needle is pulled from the needle set and the dilator sheath and catheter are pushed down the guidewire and positioned above the right atrium of the heart. The guidewire is removed, followed by the dilator sheath, so that only the catheter remains in place in the patient. A pacemaker lead is fed into the catheter and threaded into the right atrium of the heart. Once the lead is in proper position, the catheter is removed.

The foregoing procedure involves a number of steps that are labor intensive. In particular, the procedure includes insertion and removal of many separate components. In addition to being labor intensive, the procedure poses safety risks to the medical professional. When the needle is removed from the needle set, it is contaminated. The handling of such used needles poses a risk of transmission of various pathogens, including human immunodeficiency virus (HIV), due to inadvertent needle sticks.

SUMMARY OF THE INVENTION

Based on the foregoing, the present invention provides a medial device that allows a safer and more simplified method for percutaneous insertion of medical instruments, such as pacemaker leads. The device is intended for insertion into any medium or large diameter blood vessel accessible through the skin. For purposes of this disclosure, the device will be discussed as it is used in the insertion of pacemaker leads. The device includes a sharpened flexible needle surrounded by a dilator sheath, both of which extend from a housing. A catheter is detachably connected to the front end of the housing over the needle and dilator sheath. A flashback chamber is fixed to the rear end of the housing.

When the flexible needle is inserted, access to the vein is verified by the appearance of blood in the flash chamber. Once the vein is accessed, the needle is retracted into the dilator sheath where it is safely enclosed for the remainder of the procedure. The flexible dilator sheath and catheter are deformed into alignment with the axis of the subclavian vein and advanced down the subclavian vein to a position above the right atrium of the heart. Since the needle is flexible, it can bend with the dilator sheath and catheter and need not be removed during the insertion procedure. The housing, dilator sheath and retracted needle are pulled out of the patient, leaving the catheter in the patient. The dilator sheath encloses the contaminated needle so that the sheath and needle can be safely discarded with minimal risk of accidental needle sticks. A pacemaker lead is then fed through the catheter in the subclavian vein and advanced into the heart. Once the lead is in place, the catheter is removed from the patient, and the lead is connected to a pacemaker device.

DESCRIPTION OF THE DRAWINGS

The foregoing summary as well as the following description will be better understood when read in conjunction with the figures in which.

DETAILED DESCRIPTION OF THE PREFERRED EMBODIMENT

Figure 1:
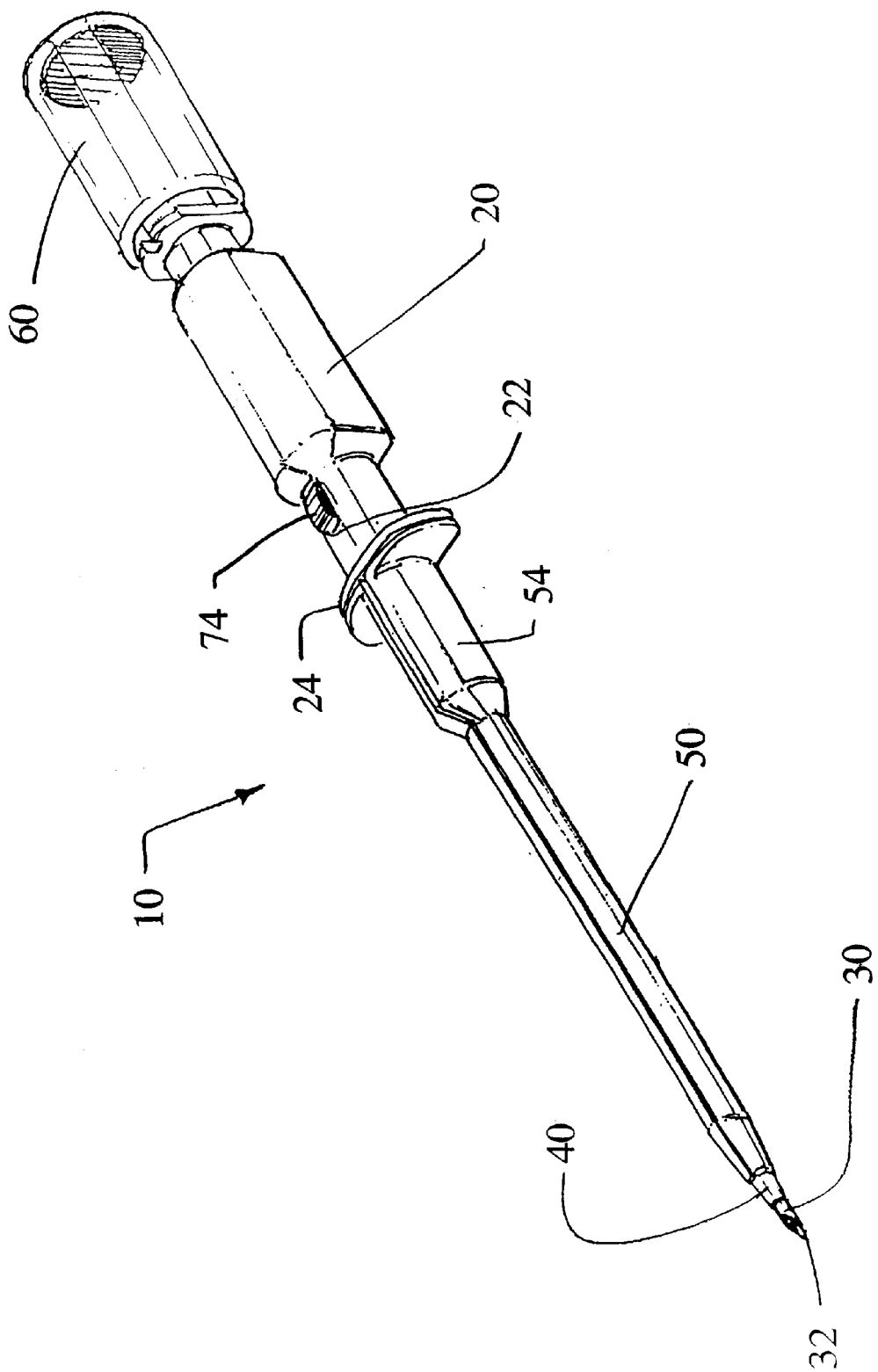
FIG. 1 is a perspective view of a medical device having a retractable flexible needle.

Referring now to the figures in general and to FIG. 1 specifically, a medical device for inserting medical instruments, such as pacemaker leads, into a patient is designated generally 10. The device 10 includes a sharpened flexible needle 30 inside a catheter 50 and dilator sheath 40. The flexible needle 30 can access a blood vessel and be bent or curved into alignment with the blood vessel. After the blood vessel is accessed, the needle is retracted into the device 10 to enclose the contaminated needle tip. The catheter 50 is advanced into position above the heart, and the needle and dilator are removed, leaving the catheter in place. A pacemaker lead is then threaded through the catheter and into the heart.

Figure 2:
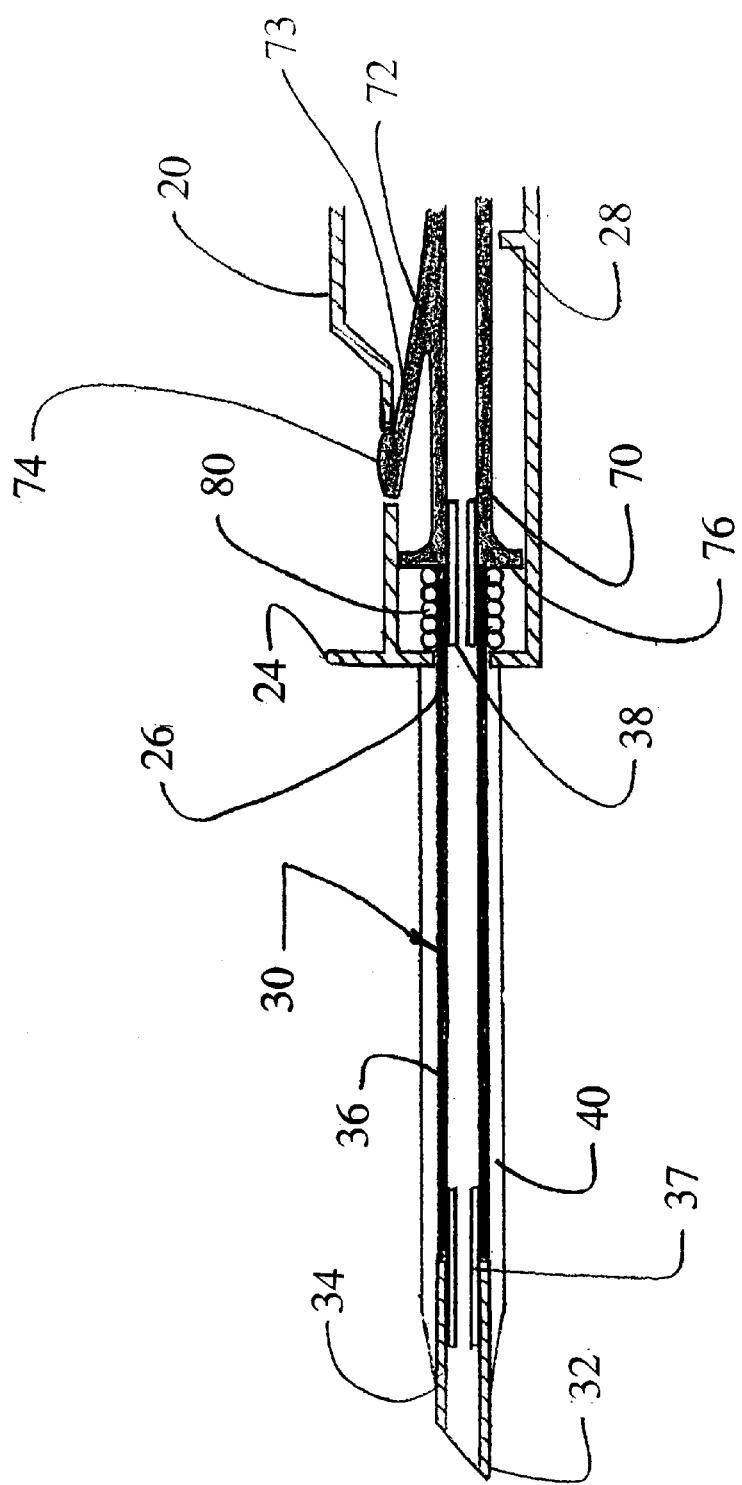
FIG. 2 is a fragmentary cross-sectional view of the medical device in FIG. 1, illustrating the needle in the extended position.

Referring now to FIG. 1, the device includes a generally cylindrical housing 20 and a flexible needle 30 extending forwardly from the housing. The flexible needle 30 is surrounded by a dilator sheath 40 slidably disposed within the catheter 50. Once the catheter 50 is properly positioned in the patient, the housing 20, needle 30 and sheath 40 are detached from the catheter and removed from the patient. FIG. 2 shows the device with the catheter 50 removed. The rearward end of needle 30 is attached to a needle hub 70 disposed within housing 20. A spring 80 disposed within the housing 20 biases the needle hub 70 rearwardly toward a retracted position. A needle retainer 72 releasably retains needle hub 70 against the bias of spring 80. The medical professional using the device 10 can retract flexible needle 30 by pressing a button 74, which disengages the needle retainer 72. The spring 80 then propels needle 30 rearwardly so that the sharpened tip of needle 30 is enclosed within the sheath 40.

The needle 30 and sheath 40 can be removed from the catheter 50 by sliding the needle and sheath out of an opening at the rearward of the catheter. Once the needle 30 and sheath 40 are removed, a pacemaker lead can be inserted through the catheter 50 and into the blood vessel.

Figure 3:
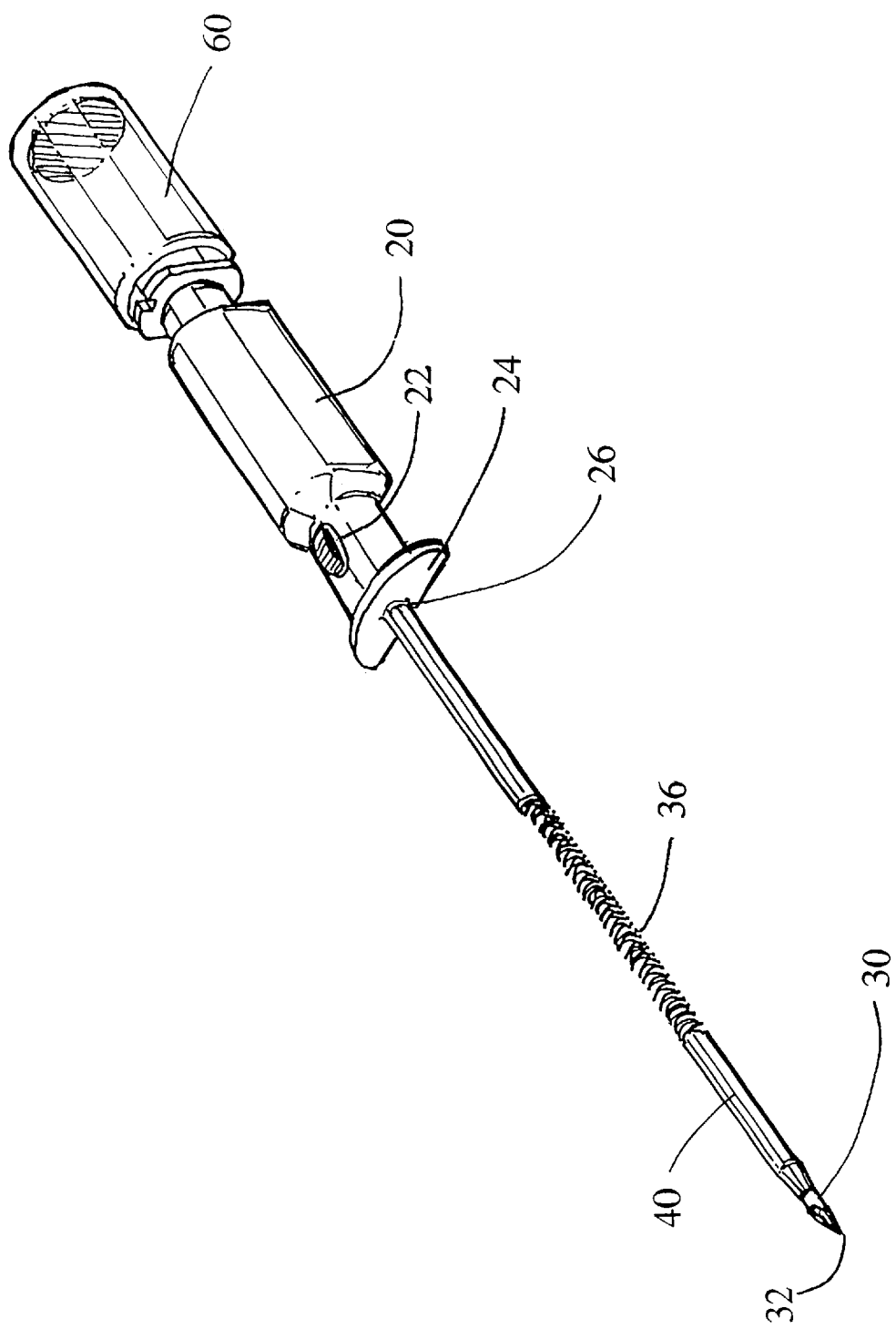
FIG. 3 is a perspective view of the medical device in FIG. 1 with a catheter removed and showing a cut-away view of a portion of the flexible needle.

Referring to FIGS. 2–3, the details of the device 10 will now be explained in greater detail. The housing 20 is a generally cylindrical barrel having a hollow central bore. The housing 20 has an open rearward end and a flange 24 at its forward end. The flange 24 extends outwardly from the housing in a direction perpendicular to the longitudinal axis of the housing so as to form a pair of finger grips, as will be explained later. The front end of the housing 20 includes a circular opening 26 generally centered in axial alignment with the bore of the housing 20. The rear end of needle 30 is connected to the needle hub 70 inside the housing 20 and extends forwardly through opening 26 so that the front sharpened tip 32 extends forwardly outside the housing. The rear end of dilator sheath 40 is fixedly connected to the flange 24 over the opening 26. The sheath 40 extends forwardly in axial alignment with the needle 30 so as to substantially cover the needle shaft.

The open rearward end of the housing 20 is configured to engage with a blood collection device in fluid communication with the needle. For example, the rearward end of the housing 20 may be connected to a vial or a syringe. In FIGS. 1 and 3, the rearward end of the housing 20 is connected to a fluid chamber referred to as a flash chamber 60 so that blood flowing through the needle enters the flash chamber. The flash chamber 60 may be connected to housing 20 in a variety of ways, including bonding or a threaded connection. Alternatively, the rear end of housing 20 may have a luer fitting.

A locking aperture 22 is located in the sidewall toward the front end of housing 20. The aperture 22 cooperates with the needle retainer 72 as explained further below.

Figure 8:
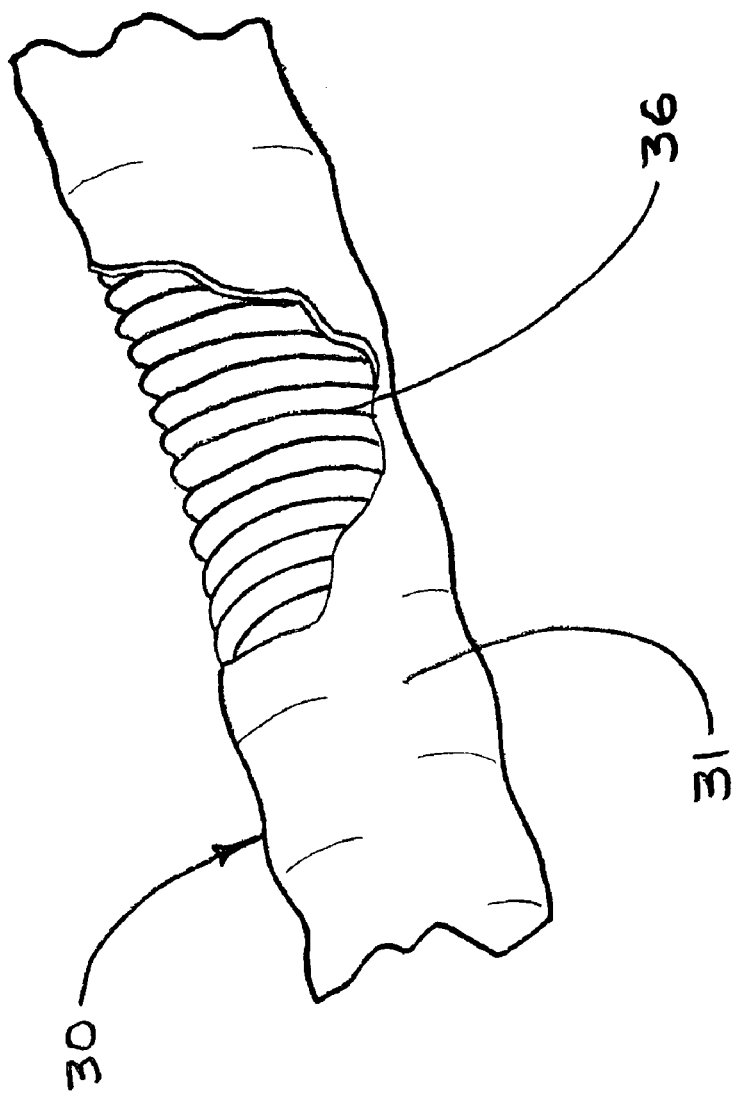
FIG. 8 is an enlarged fragmentary cut-away view of the medical device in FIG. 3 taken from the circled section in FIG. 3 labeled "FIG. 8".
Figure 3:
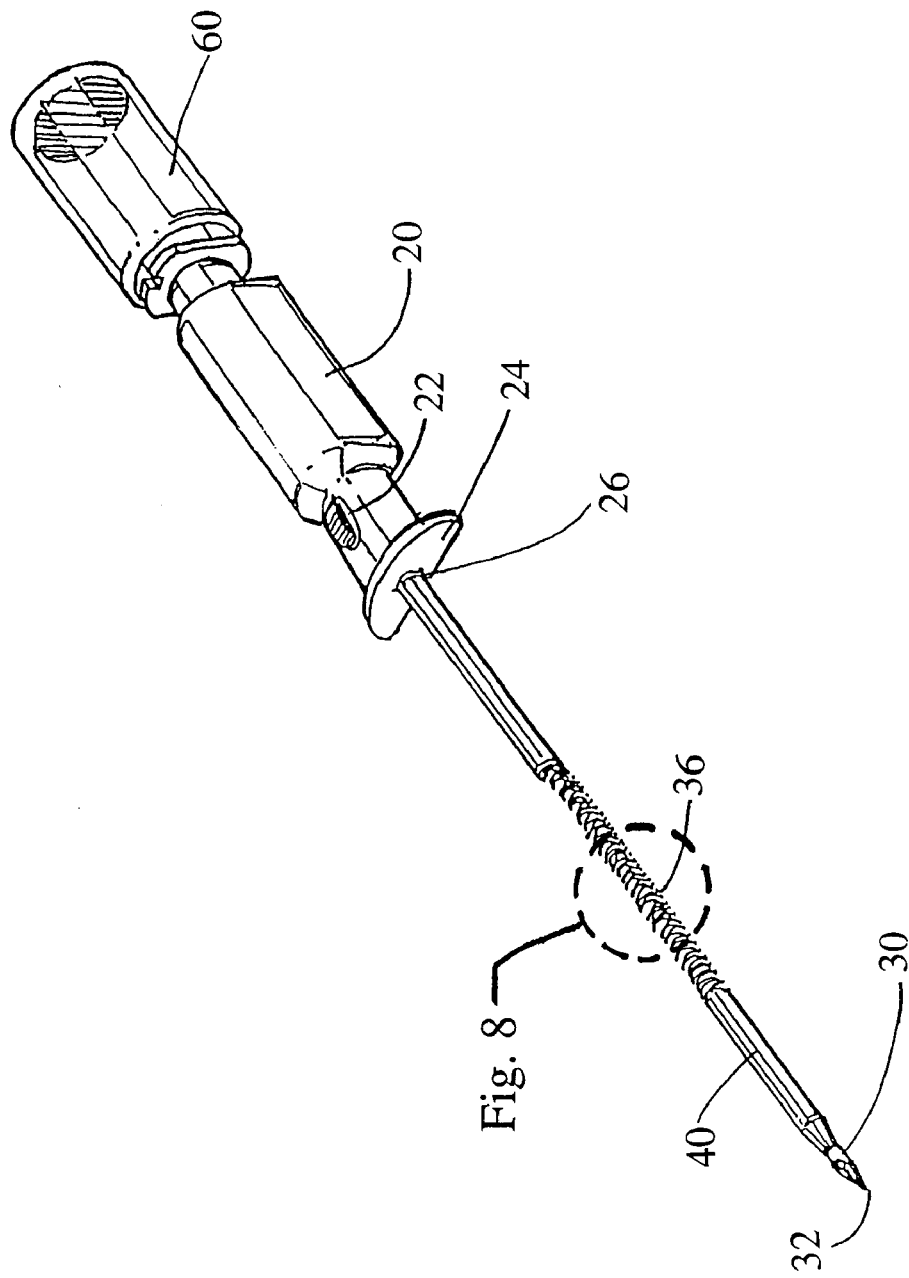
Figure 8:
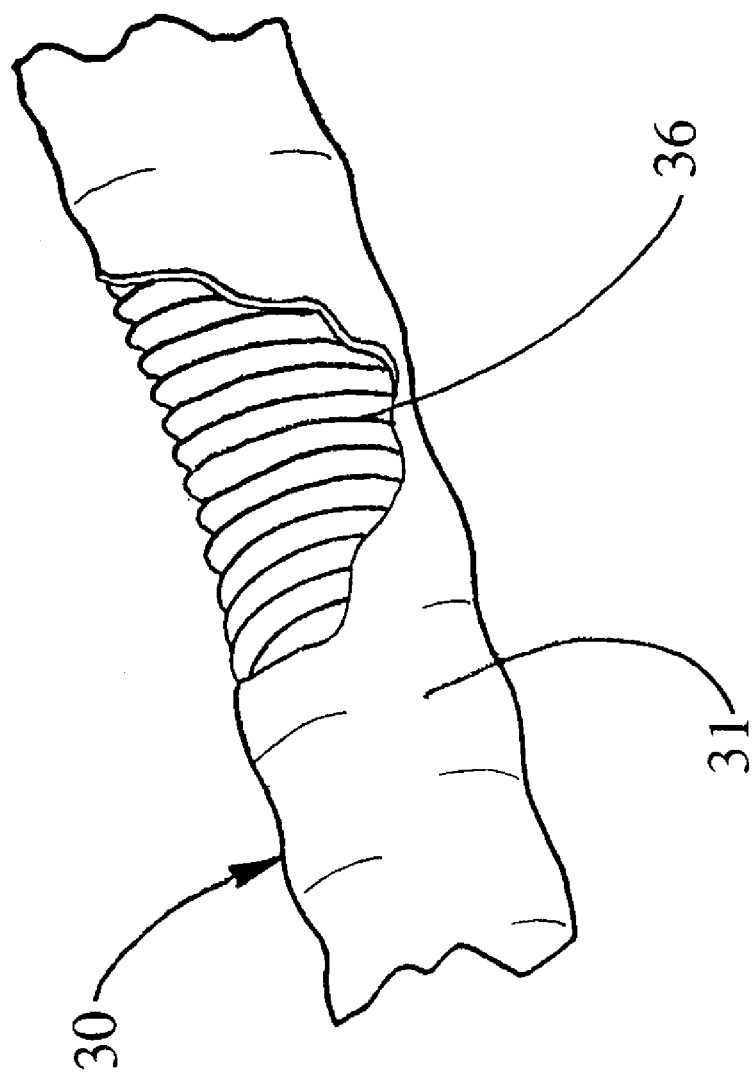

Referring again to FIGS. 2–3, the details of the flexible needle 30 are illustrated. The flexible needle 30 includes a cylindrical needle head 34 and a cylindrical needle body 36 attached to the rearward end of the needle head. The interior diameter of needle head 34 is substantially equal to the interior diameter of needle body 36 so as to form a uniform diameter fluid conduit. The needle body 36 is formed of a closely wound wire coil that allows the needle 30 to bend and flex to facilitate easy alignment of the needle and sheath with the subclavian vein. In this way, the body 36 is substantially more flexible than the needle head 34 which is generally rigid. Referring now to FIG. 8, the wound wire coil is tightly wound so as to be fluid tight. In addition, the exterior of the coil is coated with a low-friction polymer coating 31, such as Teflon, to provide a smooth exterior so as to reduce friction as the sheath 40 slides over the needle 30. The coating also maintains the fluid-tight characteristic of the needle 30 when the needle body is bent. Alternatively, the needle body 36 may be enclosed in a plastic jacket to retain a fluid-tight seal when the needle is bent.

A pair of hollow tubes 37, 38 connect the needle head 34, needle body 36 and needle hub 70 together. Tubes 37, 38 have reduced exterior diameters that are slightly less than the interior 2 diameter of the needle head 34, needle body 36 and needle hub 70. Tube 37 is disposed in the rear end of the needle head 34 and the front end of the needle body 36, and bonded or spot welded in place so as to form a coupling between the needle head and needle tip. Tube 38 is disposed in the rear end of needle body 36 and front end of needle hub 70 and bonded or molded in place to form a coupling between the needle body and needle hub. Tubes 37, 38 include hollow central bores so as to form a fluid conduit through needle 30.

The needle hub 70 is generally cylindrical having an internal bore for receiving needle 30. Preferably, needle hub 70 is integrally formed with needle retainer 72. The needle retainer 72 includes an axially elongated radially deformable arm 73 that extends outwardly from the needle hub 70. A button 74 projects from the end of arm 73 and is configured to cooperate with aperture 22 in the housing so as to releasably engage the needle hub 70 with the housing. The forward end of the needle hub 70 flares outwardly, forming an enlarged head 76 or flange.

Figure 4:
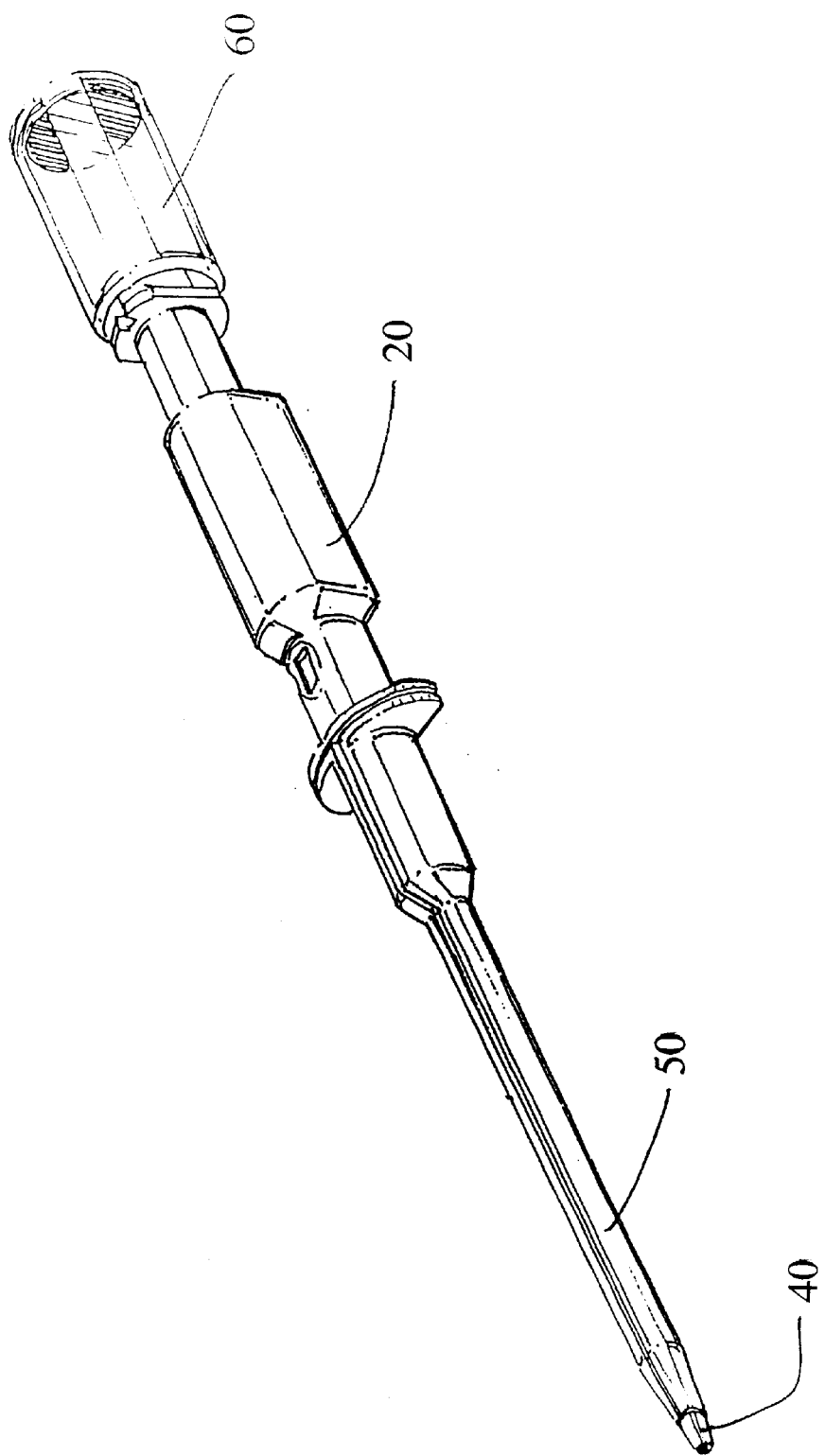
FIG. 4 is a perspective view of the medical device in FIG. 1, showing the device with the needle retracted.

As mentioned earlier, the needle 30 is operable between a projecting position and a retracted position. In the projecting position, shown in FIG. 1, the needle 30 projects forwardly from the housing 20 so that the sharpened tip 32 is exposed forwardly of sheath 40 to pierce a patient. In the retracted position, shown in FIG. 4, the sharpened tip 32 of needle 30 is disposed within the sheath 40. The spring 80 biases the needle 30 rearwardly toward the retracted position. The needle retainer 72 releasably retains the needle 30 in the projecting position against the bias of the spring 80.

Referring again to FIGS. 1–2, the needle 30 is retained in the projecting position against the bias of the spring 80 as follows. The button 74 is biased radially outwardly so as to project outwardly through aperture 22. The spring 80 biases the needle hub 70 rearwardly, such that the radial arm and button 74 extending from the needle hub are also biased rearwardly. The rearward and radial bias on the button 74 holds the button in engagement with the rim of the aperture 22, preventing rearward displacement of the needle hub 70 and needle 30. The button 74 is disengaged from the rear side of aperture 22 by pressing the button radially inwardly.

A stop limits the rearward travel of needle hub 70, and more specifically limits the distance that the needle 30 can be retracted. The housing includes a tab 28 projecting radially inwardly from the interior surface of the housing, intermediate the length of the housing. The tab 28 forms a stop that engages the enlarged head 76 on the needle hub 70 to substantially impede rearward displacement of the enlarged head 76 beyond the tab. Rearward displacement of the needle hub 70 and the needle 30 during retraction is limited so that the needle is not displaced out of the housing. In this way, the rearward end of the contaminated needle cannot be accessed after retraction. Accordingly, the needle 30 is substantially permanently enclosed within the sheath 40 and housing 20 and cannot be re-extended.

The needle 30 extends through the central bore of the needle hub 70, and through the opening 26 in the front of housing 20 so that the sharpened tip 32 extends forwardly from the housing. The sheath 40 is fixedly attached to the front end of housing 20 in axial alignment with the needle 30 so that the sheath also projects forwardly from housing. The sheath 40 may be attached to the front end of the housing 20 by bonding or by being molded to the housing.

The sheath 40 is in the form of a flexible thin-walled cannula overlying the needle 30 in telescoping relation so that the needle and sheath are co axial. The interior diameter of sheath 40 is substantially the same as the external diameter of needle 30. Preferably, the interior diameter of sheath 40 is the same as or a few thousandths of an inch larger than the external diameter of the needle 30, so that the needle can readily slide within the sheath.

After use, the sheath 40 shields the sharpened tip of the needle 30 against inadvertent contact. Preferably, the sheath 40 is somewhat flexible. In addition, the sheath is preferably formed with sufficient column strength to prevent the sheath 40 from collapsing axially in response to an axial force after retraction. This columnar strength prevents the sheath from readily buckling axially after retraction, which could expose the contaminated needle. In other words, the sheath 40 is preferably laterally flexible, but is substantially axially incompressible. In addition, preferably the sheath is substantially puncture resistant, so that the needle will not puncture the sheath if the sheath buckles or compress. In this way, the sheath protects the contaminated needle after retraction. In the present instance the sheath is formed of Teflon. However, a variety of other known plastic materials, such as polyurethane, may be used to form the sheath.

Referring to FIGS. 1–3, the forward end of the sheath 40 tapers inwardly so as to form a frustoconical end. The frustoconical end of sheath 40 tapers radially inwardly so that the exterior diameter of the forward end of the sheath is slightly larger than the exterior diameter of needle 30. As such, the forward end of the sheath forms a bevel providing a smooth transition is formed between the needle tip 32 and the frustoconical end of the sheath 40. Therefore, when the needle tip 32 pierces the skin of a patient, the overlying sheath 40 readily penetrates and dilates the tissue.

The catheter 50 is generally cylindrical and has a rearward end that is flanged so as to coincide with the front flange 24 on the housing 20, as shown in FIG. 1. The catheter 50 has a bore configured to fit over the dilator sheath 40 so that the catheter and sheath are substantially coaxial. When the catheter 50 is disposed over the sheath 40, the rearward end of catheter 50 and front flange 24 of housing 20 form a pair of flaps that serve as finger grips. The frustoconical front end of sheath 40 projects outwardly from the front end of the catheter. Preferably, the interior diameter of the catheter 50 is the same as or a few thousandths of an inch larger than the external diameter of sheath 40 so that the sheath and catheter are held together in frictional engagement. As with the sheath 40, the forward end of the catheter 50 tapers radially inwardly to form a frustoconical beveled front end. The tapered front end of the catheter 50 is slightly larger than the exterior diameter of the sheath 40, forming a smooth transition between the sheath and the catheter. When the needle 30 and sheath 40 are inserted into the skin or tissue of a patient, the catheter 50 readily passes through and dilates the skin or tissue with minimal resistance.

The catheter 50 is formed by a pair of axially symmetrical sections or leaves 54 that are detachably connected. More specifically, catheter 50 includes a pair of opposing leaves 54 that are symmetrical about the longitudinal axis of the catheter. The leaves 54 are separated by a breakaway connection running through the catheter walls that allows the leaves to be split or peeled apart from one another.

As discussed earlier, during use the needle tip 32 is retracted into the sheath 40. Since the entire length of needle 30 does not retract into housing 20, the length of the housing can be reduced. Preferably, the axial distance between enlarged head 76 on needle hub 70 and the stop 28 in the housing is less than one quarter of the length of needle 30.

Configured in this way, the device 10 is preferably used to insert a pacemaker lead as follows. The needle 30 pierces the skin or tissue of the upper chest of a patient. As the needle 30 is advanced into the patient, the frustoconical ends of dilator sheath 40 and catheter 50 enter the needle puncture. The needle 30, sheath 40 and catheter 50 are then advanced into the subclavian vein. Upon access of the subclavian, blood from the vein will enter the needle 30 and appear in the flashback chamber 60 to indicate that the vein has been pierced. The medical professional then presses the button 74 into the housing 20. The needle retainer 72 is thereby displaced radially inwardly out of engagement with the aperture 22 so that the spring 80 displaces the needle 30 to the retracted position within sheath 40. The sheath 40 encloses the needle tip 32 to prevent the tip from piercing or coring the vein as the device is advanced into the patient.

After needle retraction, the sheath 40 and catheter 50 are bent or curved into alignment with the direction of the subclavian vein. During this maneuver, the retracted needle 30 remains in the sheath and bends with the sheath and catheter. Preferably, substantially the full lengths of the sheath 40 and catheter 50 are advanced down the subclavian vein toward the heart after the needle is retracted. The flexible needle 30 provides additional columnar strength, reinforcing the sheath and catheter to allow the sheath and catheter to be advanced without significant buckling in the vein. Therefore, there is no need to use a guidewire to guide the sheath and catheter. The flash chamber 60 remains in place at the rear end of the housing, reducing the medical professional's exposure to the patient's blood.

Once the catheter is completely inserted into the appropriate position, the medical professional detaches the housing from the catheter by holding the catheter in place with one hand and pulling the housing outwardly with the other hand until the sheath 40 and retracted needle 30 are pulled out of the catheter. As stated earlier, the needle tip is safely enclosed within the sheath 40, so as to minimize the risk of an inadvertent needle stick. The contaminated needle 30, sheath 40 and housing 20 are safely discarded after being removed from the catheter 50.

The catheter 50 remains in the patient, with its rearward end open to receive a pacemaker lead. Blood may continue to flow through catheter 50 after the housing 20, sheath 40 and needle 30 are detached. Therefore, the medical professional may control this flow by sealing the port with his or her finger until he or she is ready to insert the pacemaker lead. The pacemaker lead is fed through the catheter port and advanced into the heart area. Once the lead is in the proper position, the medical professional slides the catheter end out of the patient, and splits or pulls apart the catheter leaves 54 radially outwardly to remove the catheter from the pacemaker lead. The inserted pacemaker lead is then ready to be connected to a pacemaker device.

Figure 5:
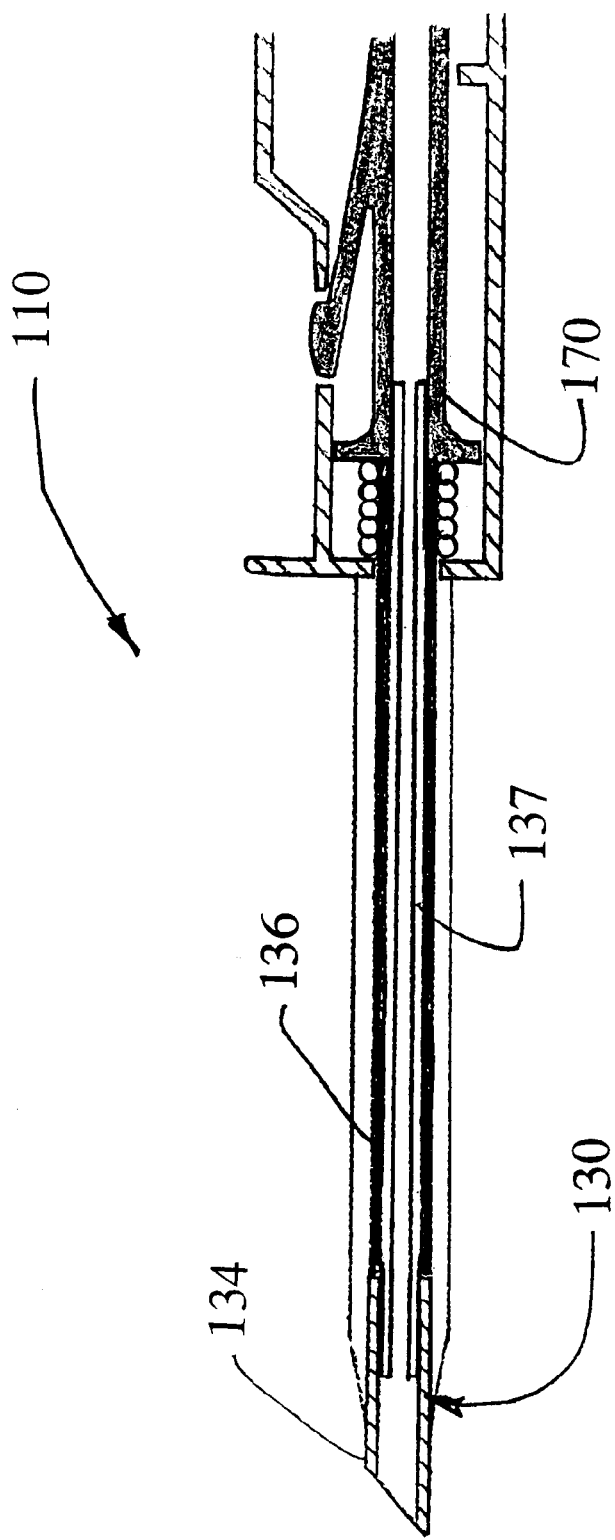
FIG. 5 is a fragmentary cross-sectional view of a second embodiment of a medical device having a retractable flexible needle.

Referring now to FIG. 5, a second embodiment of a medical device 110 is shown with a modified flexible needle 130. The other elements of the device 110 are substantially similar to the elements of the first device 10 described above. In addition, the method of using the device 110 is substantially similar to the method of using the first device 10 described above.

The flexible needle 130 includes a hollow needle tip 134, hollow needle body 136 and needle hub 170. As in the first embodiment, the needle body 136 is formed of Teflon-coated wound wire. The needle tip 134, needle body 136 and needle hub 170 are interconnected by a single telescopic tube 137 within the needle body that runs substantially the entire length of the needle body. As such, the needle body 136 may be slightly more rigid than the needle discussed above in the first embodiment.

Figure 6:
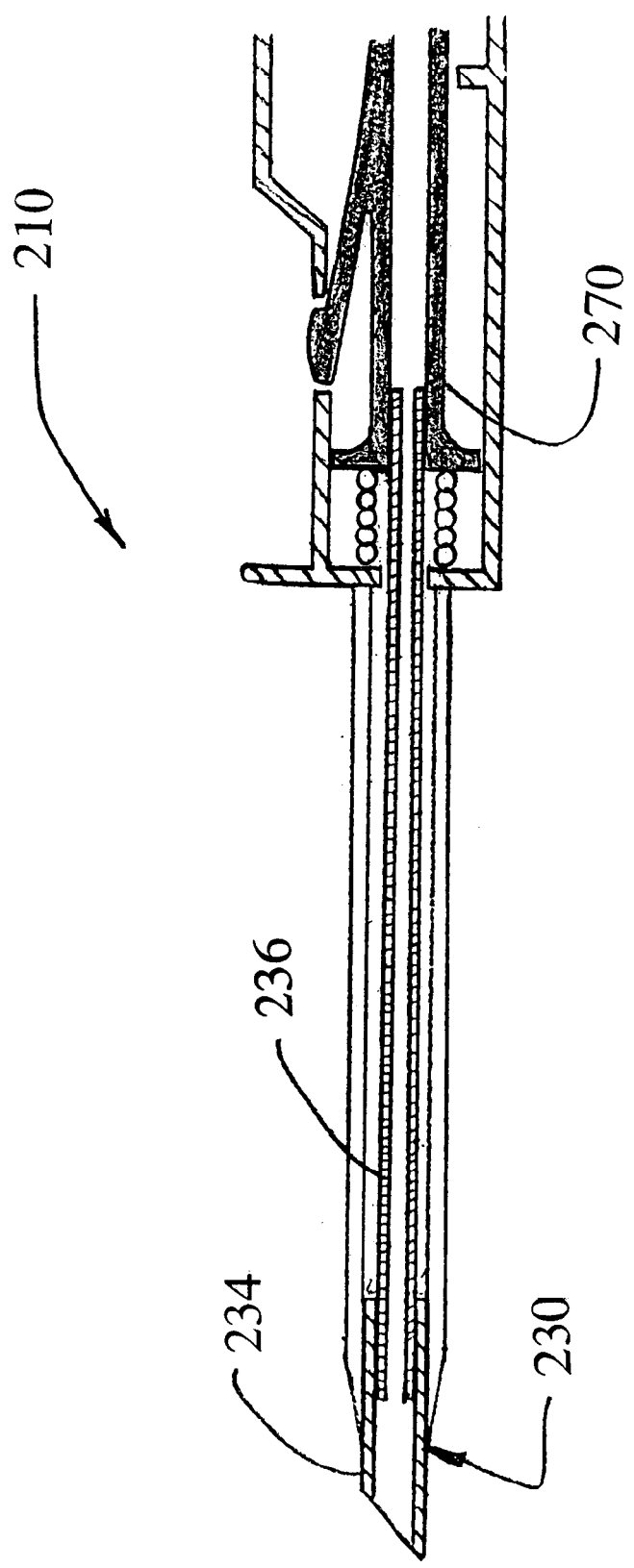
FIG. 6 is a fragmentary cross-sectional view of a third embodiment of a medical device having a retractable flexible needle.

FIG. 6 shows a third embodiment of a medical device 210 having a modified flexible needle 230. The other elements of the device 210 and method of use are substantially similar to the elements of the first device 10 and method of use described above.

The flexible needle 230 includes a needle tip 234 and a hollow needle body 236 formed from a reduced diameter tubing. The tubing may be formed of any semi-rigid material, such as steel commonly used in the manufacturing of needles. The front end of needle body 236 is disposed in the rear end of needle tip 234, and fixedly connected to the needle tip by bonding, swaging or spot welding. The rear end of needle body 236 is fixedly connected to a needle hub 270, either by bonding or molding the needle body to the needle hub. The ratio of the outside diameter to the inside diameter of the needle body 236 is relatively small, such that the needle body has a relatively thin wall. In this way, as in the earlier embodiments, the needle body 236 is substantially more flexible than the needle tip 234. Using such a thin walled needle body 234 provides a flexible body that is less costly than the Teflon-coated wound coils used in the first and second embodiments.

Figure 7:
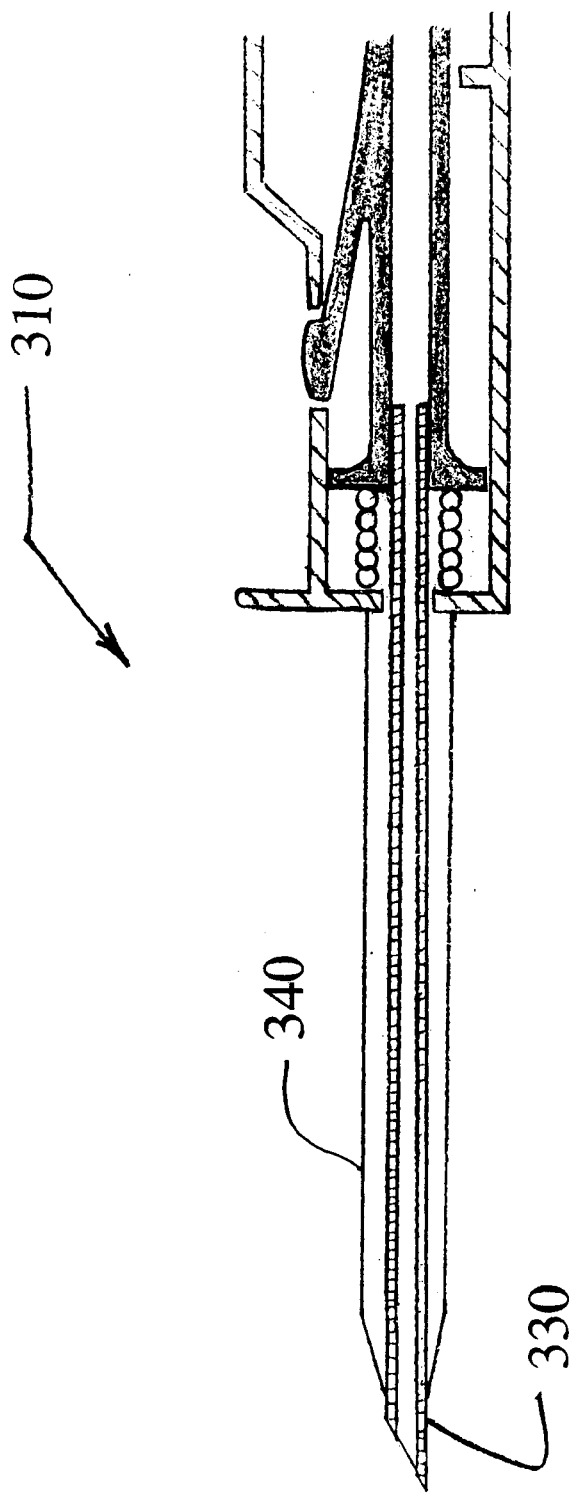
FIG. 7 is a fragmentary cross-sectional view of a fourth embodiment of a medical device having a retractable flexible needle.

Referring now to FIG. 7, a fourth embodiment of needle device 310 is shown having a single component needle 330 surrounded by a dilator sheath 340. The other elements of device 310 and method of use are substantially similar to the first device 10 described above. The needle 330 has a reduced ratio between its outside diameter and inside diameter to provide a thin-walled needle. The reduced wall thickness in needle 330 gives the needle a lower resistance to bending, increasing the overall flexibility of device 310. As needle 330 is inserted into a patient's skin or tissue, columnar strength is provided by the dilator sheath 340, which allows the needle to penetrate the skin without excessive buckling or breaking. As in the previous embodiments, after insertion, the needle 330 is retracted into the sheath. The flexibility of the needle 330 allows the device to then be further inserted into the patient and manipulated as described previously.

Since the needle 330 is made up of a single component, the needle requires no assembly and is cheaper to manufacture than the needles described in the previous embodiments. Moreover, the needle 330 does not require sealing between components, as is required in the previous embodiments.

The terms and expressions which have been employed are used as terms of description and not of limitation. There is no intention in the use of such terms and expressions of excluding any equivalents of the features shown and described or portions thereof. It is recognized that various modifications are possible within the scope and spirit of the invention. For instance, the device 10 has been described in connection with the insertion of pacemaker leads. However, the device can be used for inserting a variety of items vascularly into the patient. Accordingly, the invention incorporates variations that fall within the scope of the following claims.

What is claimed is:

1. A medical device for inserting a medical instrument, comprising:

a housing;

a flexible needle disposed in the housing and having a sharpened tip;

a sheath disposed around the flexible needle;

a needle retainer disposed in the housing;

a biasing element;

a catheter attached to the front end of the housing; and an actuator, wherein, after the sharpened tip of the needle is inserted into a patient's blood vessel, operation of the actuator causes relative displacement of the needle so that the sharpened tip of the needle is enclosed within the sheath, whereafter the enclosed needle, the sheath and the catheter may be curved into alignment with the blood vessel, and the needle and the sheath subsequently removed so as to provide clearance for the medical instrument to be inserted through the catheter and into the blood vessel.

2. The medical device of claim 1, wherein the needle is operable between an extended position in which the sharpened tip projects forwardly from the front end of the sheath, and a retracted position, wherein the sharpened tip is enclosed within the sheath.

3. The medical device of claim 2, wherein the biasing element biases the needle toward the retracted position.

4. The medical device of claim 3, wherein the needle retainer releasably retains the sharpened tip of the needle in the extended position against the force of the biasing element.

5. The medical device of claim 4, wherein the actuator releases the needle retainer so as to allow the sharpened tip of the needle to be displaced from the extended position to the retracted position.

6. The medical device of claim 1, wherein the housing further comprises a blood collection component.

7. The medical device of claim 6, wherein the blood collection component is one of a syringe or a flash chamber.

8. The medical device of claim 1, wherein the biasing element is a compression spring disposed in the front end of the housing.

9. The medical device of claim 1, wherein the actuator comprises a hub that projects through an aperture in the wall of the housing.

10. The medical device of claim 1, wherein the flexible needle is comprised of:

a hollow needle tip;

a flexible closed wound polymer-coated wire; and a telescopic tube connector disposed within the needle tip and closed wound wire that connects the needle tip to the closed wound wire.

11. A medical device comprising:

a flexible needle having a sharpened tip a sheath disposed around the needle, such that the sharpened tip projects forwardly from the sheath when the needle is in an extended position.

a biasing element biasing the needle rearwardly toward a retracted position in which the sharpened tip is shielded within the sheath against inadvertent contact.

a needle retainer releasably retaining the needle in the extended position against the rearward bias of the biasing element.

wherein after retraction of the needle, the sheath and enclosed needle are laterally flexible to allow the needle and sheath to be bent after insertion into a patient.

12. The medical device of claim 11 wherein the needle comprises a closely wound wire forming a plurality of overlapping convolutions facilitating lateral resilient deformation of the needle.

13. The medical device of claim 12 comprising a needle liner having a low coefficient of friction.

14. The medical device of claim 13 wherein the needle liner comprises a polymer coating.

15. The medical device of claim 12 wherein the needle comprises a sharpened tip fixedly attached to the wire.

16. The medical device of claim 11 comprising a catheter disposed about the sheath wherein the catheter is releasably engageable with the sheath.

17. The medical device of claim 11 comprising a fluid reservoir in fluid communication with the needle.

18. The medical device of claim 11 comprising a housing fixedly attached to the sheath, wherein the biasing element is disposed within the housing.

19. The medical device of claim 11 wherein the sheath has a beveled forward edge providing a smooth transition between the needle and the overlying sheath.

20. The medical device of claim 11 wherein the needle retainer comprises a radially displaceable arm fixedly attached to the needle.

* * * * *

UNITED STATES PATENT AND TRADEMARK OFFICE
CERTIFICATE OF CORRECTION

PATENT NO.     : 6,607,511 B2
DATED          : November 7, 2003
INVENTOR(S)    : Halseth et al.

It is certified that error appears in the above-identified patent and that said Letters Patent is hereby corrected as shown below:

Drawings,
Sheet 3, Figure 3, should be replaced with the attached.
Sheet 8, Figure 8, should be replaced with the attached.

Signed and Sealed this

Twenty-fourth Day of August, 2004

JON W. DUDAS
*Director of the United States Patent and Trademark Office*